United States Patent
Li et al.

(10) Patent No.: US 11,564,658 B2
(45) Date of Patent: Jan. 31, 2023

(54) ULTRASOUND ELASTOGRAPHY IMAGING SYSTEM AND METHOD

(71) Applicants: SHENZHEN MINDRAY BIO-MEDICAL ELECTRONICS CO., LTD., Shenzhen (CN); RUIJIN HOSPITAL, SCHOOL OF MEDICINE, SHANGHAI JIAOTONG UNIVERSITY, Shanghai (CN)

(72) Inventors: Shuangshuang Li, Shenzhen (CN); Jianqiao Zhou, Shanghai (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 352 days.

(21) Appl. No.: 15/894,476

(22) Filed: Feb. 12, 2018

(65) Prior Publication Data
US 2019/0046160 A1    Feb. 14, 2019

Related U.S. Application Data

(63) Continuation of application No. PCT/CN2015/086531, filed on Aug. 10, 2015.

(51) Int. Cl.
*A61B 8/08*    (2006.01)
*A61B 8/00*    (2006.01)
(Continued)

(52) U.S. Cl.
CPC ............ *A61B 8/485* (2013.01); *A61B 8/5223* (2013.01); *B06B 1/0215* (2013.01); *B06B 3/00* (2013.01);
(Continued)

(58) Field of Classification Search
CPC .... C12Q 1/686; C12Q 1/6883; C12Q 1/6886; C12Q 2600/156; C12Q 2600/16;
(Continued)

(56) References Cited

U.S. PATENT DOCUMENTS 6,482,159 B1 *   11/2002   Wiesauer ................. A61B 8/06
                                                        128/916
8,734,351 B2 *   5/2014    Waki ........................ A61B 8/08
                                                        600/442
(Continued)

FOREIGN PATENT DOCUMENTS

CN     101065067 A     10/2007
CN     103037771 A     4/2013
(Continued)

OTHER PUBLICATIONS

Carlsen et al (A Comparative Study of Strain and Shear-Wave Elastography in an Elasticity Phantom, American Roentgen Ray Society, AJR:204, W236-W242, Mar. 2015) (Year: 2015).*

*Primary Examiner* — Yi-Shan Yang
*Assistant Examiner* — Alexei Bykhovski
(74) *Attorney, Agent, or Firm* — Kory D. Christensen

(57) ABSTRACT

The present disclosure relates to an ultrasound elastography system and method. The system may include a transmitting/receiving unit which transmits ultrasound pulses to a target and receives ultrasound echoes from the target to obtain the ultrasound echo signals; an imaging unit which processes the ultrasound echo signals and displays the obtained image; and an analysis unit which detects a region of interest and a shell region selected by an operator in the image, calculate elasticity parameters in a reference region and the shell region respectively, and analyzes the elasticity parameters to obtain an analysis result.

23 Claims, 3 Drawing Sheets

(51) Int. Cl.
*B06B 3/00* (2006.01)
*B06B 1/02* (2006.01)
*A61B 8/14* (2006.01)

(52) U.S. Cl.
CPC ............ *A61B 8/14* (2013.01); *A61B 8/461* (2013.01); *A61B 8/469* (2013.01); *B06B 2201/76* (2013.01)

(58) Field of Classification Search
CPC .......... G16B 25/00; A61B 8/14; A61B 8/461; A61B 8/469; A61B 8/485; A61B 8/5223; A61B 8/4411; A61B 8/52; A61B 8/5207; B06B 1/0215; B06B 2201/76; B06B 3/00
See application file for complete search history.

(56) References Cited

U.S. PATENT DOCUMENTS

| | | | | |
|---|---|---|---|---|
| 2010/0331694 | A1* | 12/2010 | Waki | A61B 8/08 600/443 |
| 2011/0098563 | A1* | 4/2011 | Osaka | A61B 8/08 600/438 |
| 2011/0194748 | A1 | 8/2011 | Tonomura et al. | |
| 2012/0209115 | A1* | 8/2012 | Tonomura | A61B 8/463 600/438 |
| 2012/0254747 | A1* | 10/2012 | Bocirnea | G06F 3/04845 715/702 |
| 2012/0269416 | A1* | 10/2012 | Waki | A61B 8/483 382/131 |
| 2015/0141822 | A1* | 5/2015 | Miyauchi | A61B 8/5223 600/438 |
| 2015/0279025 | A1* | 10/2015 | Waki | A61B 8/5207 382/103 |
| 2015/0289840 | A1* | 10/2015 | Konofagou | A61B 8/485 600/438 |

FOREIGN PATENT DOCUMENTS

| | | |
|---|---|---|
| CN | 103720489 A | 4/2014 |
| JP | 2009039472 A | 2/2009 |
| WO | WO 2014/198012 A1 | 12/2014 |

* cited by examiner

ULTRASOUND ELASTOGRAPHY IMAGING SYSTEM AND METHOD

CROSS-REFERENCE TO RELATED APPLICATIONS

This application is a continuation of Patent Cooperation Treaty Application No. PCT/CN2015/086531, filed Aug. 8, 2015, for "Ultrasound Elastography Imaging System and Method," which is incorporated herein by reference in its entirety.

TECHNICAL FIELD

The present disclosure relates to ultrasound imaging, particularly to an ultrasound elastography system and a method thereof.

BACKGROUND

Ultrasound electrography, which relates to the elasticity or hardness of tissue, has been a focus of clinic research in the field of ultrasound imaging in recent years. The basic principle of ultrasound elastography may be described as follows. The target tissue may be slightly compressed with a probe. Alternatively, a certain pressure to the tissue may be formed with the assistance of procedures such as the body's own breathing or vascular pulsation. Thereafter, two frames of ultrasound echo signals before and after the compression may be acquired. When the tissue is compressed, a strain along the compression direction is produced in the tissue. If the distribution of Young's modulus is uneven in the tissue, the strain distribution in the tissue may vary. The strain information of the tissue may be detected through various methods, and outputted to the display interface as elastic images. This method relies on qualitative or quantitative techniques to display elastic parameters in the region of interest, thereby forming an elasticity distribution image, and distinguishes the hardness of tissue by different gray scales or different colors in the image.

However, in most cases, only showing the elastic image may not fulfill the user's needs. The user may not only want to identify the target of interest, but also may want to make further detailed analysis for the target of interest and find more information therefrom. For example, in some applications, the hardness of infiltration area around the lesion may be one of the major objects of concern for the user.

SUMMARY

Disclosed herein is an ultrasound elastography system and an ultrasound elastography method.

BRIEF DESCRIPTION OF THE DRAWINGS

FIG. 3 is a schematic diagram which shows the expanding of a region of interest to obtain a shell region in one embodiment;

FIG. 4 is a schematic diagram which shows a shell region and a reference region in one embodiment;

DETAILED DESCRIPTION

Figure 1:
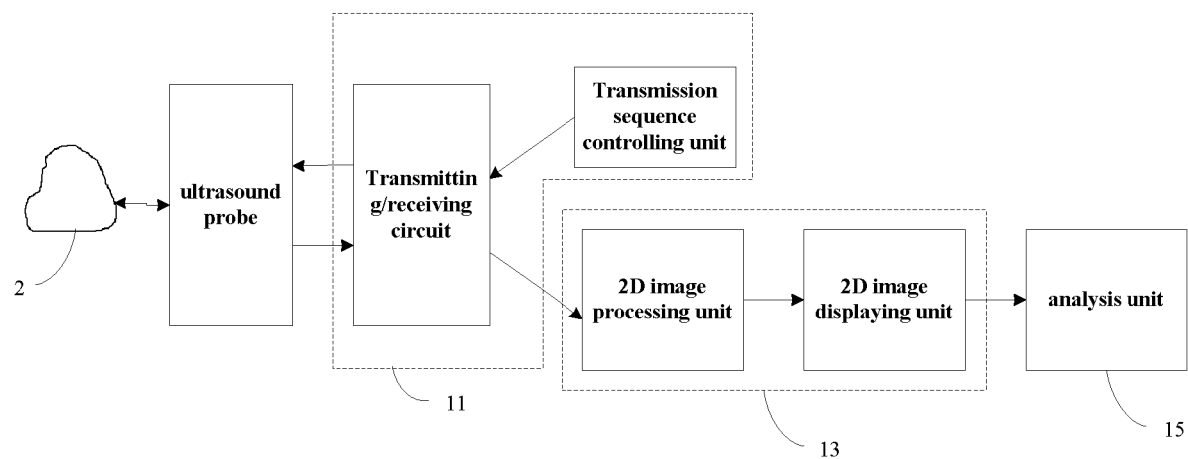
FIG. 1 is a structural schematic diagram of an ultrasound elastography system in one embodiment.

In one embodiment, an ultrasound elastography system may be provided. The system may include an ultrasound probe, a transmitting/receiving unit, an imaging unit, and an analysis unit.

The transmitting/receiving unit may excite the ultrasound probe to transmit ultrasound pulses to a target to be inspected, and receive ultrasound echoes from the target through the ultrasound probe to obtain ultrasound echo signals. The imaging unit may process the received ultrasound echo signals to obtain ultrasound images of the target and display the images obtained by the processing.

The analysis unit may detect a region of interest and a shell region in the ultrasound image and calculate elasticity parameters in a reference region and the shell region, respectively, to obtain an analysis result.

The elasticity parameters may include one or more of strain, strain ratio, strain rate, strain-time curve and elasticity histogram statistic, or any combination thereof. Alternatively, the elasticity parameters comprise one of velocity of shear wave, velocity ratio of shear wave, Young's modulus, shear modulus, Young's modulus ratio, shear modulus ratio, elasticity modulus, elasticity modulus ratio, elasticity histogram statistic, and propagation distance of shear wave, or any combination thereof.

The shell region may be a region obtained by subtracting the region of interest from an expanded region of the region of interest. Alternatively, the shell region may be a region obtained by subtracting a narrowed region of the region of interest from the region of interest. The reference region may be the region of interest. Alternatively, the reference region may be a region for reference selected by the operator in the image, or be a region preset by the system.

In one embodiment, an ultrasound elastography method may be provided. The method may include transmitting ultrasound pulses to a target to be inspected, receiving ultrasound echoes from the target to obtain ultrasound echo signals, processing the ultrasound echo signals to obtain ultrasound images of the target, and displaying the ultrasound images obtained by the processing.

The method may further include detecting a region of interest and a shell region in the ultrasound image and calculating elasticity parameters in a reference region and the shell region respectively to obtain an analysis result.

The elasticity parameters may include one or more of strain, strain ratio, strain rate, strain-time curve and elasticity histogram statistic, or any combination thereof. Alternatively, the elasticity parameters comprise one or more of velocity of shear wave, velocity ratio of shear wave, Young's modulus, shear modulus, Young's modulus ratio, shear modulus ratio, elasticity modulus, elasticity modulus ratio, elasticity histogram statistic, and propagation distance of shear wave, or any combination thereof.

The shell region may be a region obtained by subtracting the region of interest from an expanded region of the region of interest. Alternatively, the shell region may be a region obtained by subtracting a narrowed region of the region of interest from the region of interest.

The reference region may be the region of interest. Alternatively, the reference region may be a region for reference selected by the operator in the ultrasound image, or be a region preset by the system.

In one embodiment, an ultrasound elastography system may include an ultrasound probe, a transmitting/receiving unit, an imaging unit and an analysis unit.

The transmitting/receiving unit may excite the ultrasound probe to transmit ultrasound pulses to a target to be inspected, and receive ultrasound echoes from the target through the ultrasound probe to obtain ultrasound echo signals. The imaging unit may process the received ultrasound echo signals to obtain an ultrasound image of the target, and display the ultrasound image obtained.

The analysis unit may detect a region of interest and a shell region in the ultrasound image and calculate analysis parameters in a reference region and the shell region to obtain an analysis result. The analysis parameters may include one of area, diameter, distance and volume or any combination thereof. Alternatively, the analysis parameters may include one of strain, strain ratio, strain rate, strain-time curve and elasticity histogram statistic, or any combination thereof. Alternatively, the analysis parameters may include one of velocity of shear wave, velocity ratio of shear wave, Young's modulus, shear modulus, Young's modulus ratio, shear modulus ratio, elasticity modulus, elasticity modulus ratio, elasticity histogram statistic, and propagation distance of shear wave, or any combination thereof.

The shell region may be a region obtained by subtracting the region of interest from an expanded region of the region of interest or a region obtained by subtracting a narrowed region of the region of interest from the region of interest.

The reference region may be the region of interest, a region for reference selected by the operator in the ultrasound image or a region preset by the system.

In the ultrasound elastography system and method disclosed herein, after a user selects a region of interest in the image, the elasticity parameter for the shell region of the region of interest may be extracted and be compared with elasticity parameters of other regions, providing more information to the user.

In one embodiment, as shown in FIG. 1, an ultrasound elastography system may include an ultrasound probe, a transmitting/receiving unit 11, an imaging unit 13 and an analysis unit 15. The units may be implemented using any suitable combination of hardware, software, or firmware. In one embodiment, a processor may execute instructions stored in a non-transitory computer-readable medium to implement the systems and methods disclosed herein.

The transmitting/receiving unit 11 may excite the ultrasound probe to transmit pulse sequences to a target 2 to be inspected (hereinafter, referred to as the target) according to a scan rule set by a transmission sequence controlling unit, and receive ultrasound echoes reflected by the target 2 through the ultrasound probe to obtain ultrasound echo signals.

The imaging unit 13 may process the received ultrasound echo signals to obtain ultrasound images of the target and display the images obtained by the processing. In this embodiment, a two-dimensional image processing unit of the imaging unit 13 may process the received ultrasound echo signals having already been beam-formed to obtain two-dimensional ultrasound images of the target, and the two-dimensional image display unit of the imaging unit 13 may display the obtained two-dimensional ultrasound images of the target on a display device (not shown). In another embodiment, other processing operations may also be performed in the unit 13, such as signal amplification, analog/digital conversion, or orthogonal decomposition, etc. The beamforming and two-dimensional image processing involved in the imaging unit 13 may be implemented using related ultrasound technologies and will not described in detail herein.

In one embodiment, the analysis unit 15 may detect a region of interest selected by an operator and a shell region in the displayed image, calculate elasticity parameters in the region of interest and the shell region respectively, and analyze the elasticity parameters in the region of interest and the shell region to obtain an analysis result. The shell region may be a major concerned region, which may be a region in certain range corresponding to the region of interest. For example, it may be an infiltration area surrounding a lesion.

Figure 2:
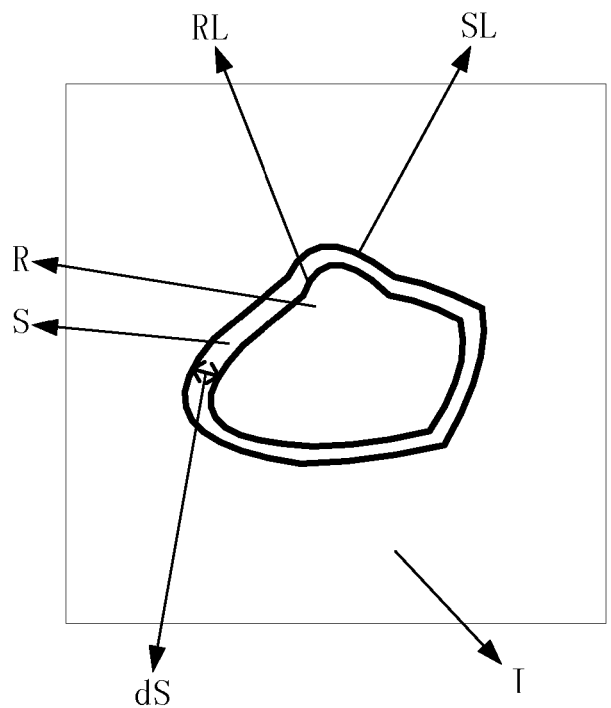
FIG. 2 is a schematic diagram which shows the expanding of a region of interest to obtain a shell region in one embodiment.
Figures 3, 4:
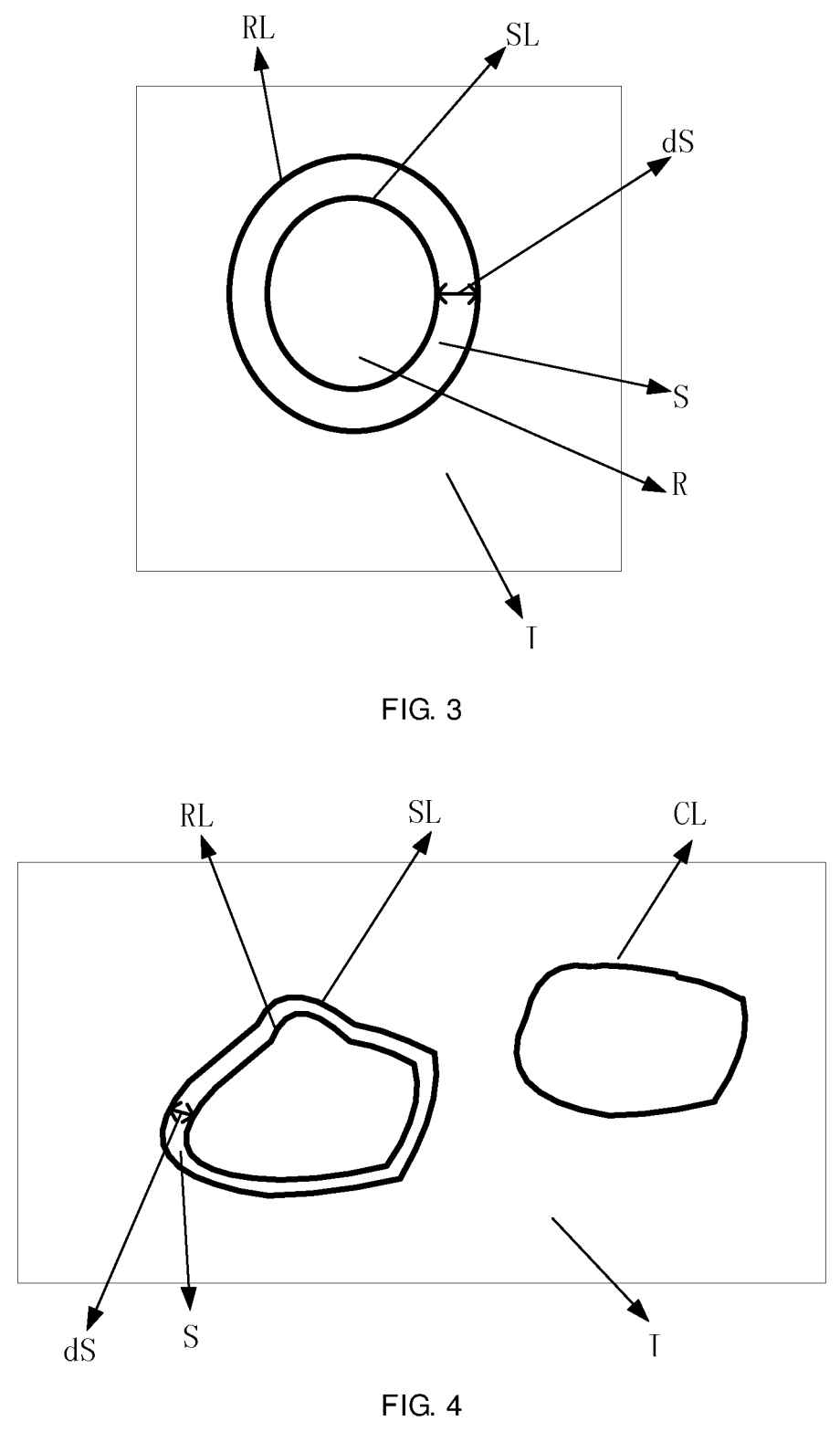

In the present embodiment, as shown in FIG. 2, the shell region S may be a region obtained by subtracting the region of interest R from an expanded region (e.g., the region surrounded by a boundary line RL) of the region of interest R in the image I. In other words, the region between the boundary line RL and the boundary line SL may be regarded as the shell region S, and the thickness of the shell region S may be dS. In another embodiment, as shown in FIG. 3, the shell region S may be a region obtained by subtracting a narrowed region (e.g., the region surrounded by a boundary line SL) of the region of interest R of the image I from the region of interest R. In other words, the region between the boundary line RL and the boundary line SL may be regarded as the shell region S, and the thickness of the shell region S may be dS. It can be seen in the FIG. 2 and FIG. 3 that the shell region may be an approximate annular region between the boundary line RL of the region of interest and the boundary line of the expanded or narrowed region of the region of interest.

The operator may select or manually draw the region of interest in the displayed image through an input device connected to the system, such as a trackball, a touch screen or a mouse. The system may provide the user a marquee tool for selection. For example, the system may provide the user an elliptical tool for selection. The user may only need to determine the position and length of the long axis and the short axis of the ellipse in order to obtain a desired elliptical region. The drawn region may be the region of interest. The system may also provide tools with other shapes for selection. The selected region of interest may be a target region with any shape and size, including regular shapes such as circle, rectangle and ellipse, and irregular shapes.

After the region of interest is obtained, the user may draw the shell region. As shown in FIG. 2 or FIG. 3, the shell region may be a region related to the expanding or narrowing of the region of interest. Similar to the region of interest, the shell region may be drawn manually by the user. Alternatively, the shell region may be drawn by the system. For example, the system may provide an option whether the shell region will be obtained by expanding or narrowing of the region of interest, and provide a selectable thickness of the shell region. The user may decide the shell region to be obtained by expanding or narrowing, and select the thickness of the shell region. Thereafter, the system may draw the shell region automatically.

In one embodiment, after obtaining the region of interest and the shell region, the analysis unit may analyze these regions, including calculating analysis parameters of these regions. The analysis parameters to be calculated may be the parameters desired to be analyzed according to the user's selection, or the parameters determined by the system by default. The analysis parameters may be general measurement parameters, such as area, diameter, distance or volume, etc., or any combination thereof. Alternatively, the parameters may also be the elasticity parameters related to elasticity of the target. The elasticity parameters may include variety of kinds according to different elastography methods. For example, in a press type elastography, the elasticity parameters may be strain, strain ratio or strain rate, etc., or any combination thereof. In a shear wave elastography, the elasticity parameters may be velocity of shear wave, velocity ratio of shear wave, Young's modulus, shear modulus, Young's modulus ratio, shear modulus ratio or propagation distance of shear wave, etc., or any combination thereof. In the present disclosure, the analysis parameters may include but not limited to strain and strain ratio, strain-time curve, velocity of shear wave and velocity ratio of shear wave, elasticity modulus and elasticity modulus ratio, and elasticity histogram statistic, etc., or any combination thereof.

For example, with regard to the strain and strain ratio, the analysis unit may calculate a mean strain of the region of interest (that is, the region inside the drawn boundary line of the region of interest), which is named as StrainMean_target, and a mean strain of the shell region, which is named as StrainMean_shell respectively, and calculate a ratio between the two, which is represented by StrainRatio=StrainMean_target/StrainMean_shell. Alternatively, the ratio may also be calculated by StrainRatio=StrainMean_shell/StrainMean_target. The ratio can represent the degree of the elasticity difference or hardness difference between the region of interest and the shell region. Under a certain pressure, the greater the tissue strain, the smaller the hardness.

Alternatively, the analysis unit may respectively calculate the strain rates (that is, the change rate of the strain over time) of the two regions and/or a ratio of the strain rates.

In one embodiment, as shown in FIG. 4, the system may additionally draw a reference region (the region enclosed by the boundary line CL as shown in the figure), calculate the mean strain or strain rate in the shell region S and the reference region, and calculate a ratio of the strains or strain rates between the two.

With regard to the strain-time curve, the analysis unit may respectively calculate the mean strain of the region of interest (StrainMean_target) and the mean strain of the shell region (StrainMean_shell) at each moment of a time period to form two strain-time curves. By displaying the two strain-time curves, the elasticity difference between the region of interest and the shell region may be analyzed, and the stability thereof within the time period may be studied.

In one embodiment, as shown in FIG. 4, the system may draw a reference region additionally, and calculate the strain-time curve of the shell region and the reference region.

With regard to the velocity of shear wave and velocity ratio of shear wave, the analysis unit may calculate a mean velocity of shear wave in the target region of interest represented as SpeedMean_target, and a mean velocity of shear wave in the shell region represented as SpeedMean_shell, and calculate a ratio named SpeedRatio between the two. The ratio can represent the degree of the elasticity difference or hardness difference between the target region of interest and the shell region. Generally speaking, the greater the shear wave velocity of tissue is, the greater the tissue's hardness will be.

In one embodiment, as shown in FIG. 4, the system may draw a reference region additionally, and calculate the velocities of shear wave and the ratio between the velocities of shear wave in the shell region and the reference region.

With regard to the elasticity modulus and elasticity modulus ratio, the analysis unit may calculate a mean elasticity modulus in the region of interest which is named as ElastoMean_target, and a mean elasticity modulus in the shell region which is named as ElastoMean_shell respectively, and calculate a ratio ElastoRatio between the two. The ratio can represent the degree of the elasticity difference or hardness difference between the region of interest and the shell region. Generally, the greater the elasticity modulus of tissue is, the greater the tissue's hardness will be. The elasticity modulus may include Young's modulus and/or shear modulus, etc.

In the press-type elastography system, the relationship between the Young's modulus E and the strain obeys the Hooke's law: stress=E*strain, where stress represents a pressure applied by the probe, and strain represents an obtained strain.

In the shear wave elastography system, the relationship between the Young's modulus E and the velocity of shear wave is proximate to $E=3\rho*Cs2$, where $\rho$ represents tissue density, and Cs represents velocity of shear wave.

The relationship between the shear modulus G and the velocity of shear wave is proximate to: $G=\rho*Cs$.

In one embodiment, as shown in FIG. 4, the system may also draw a reference region and calculate the elasticity modulus and elasticity modulus ratio in the shell region and the reference region.

With regard to the elasticity histogram statistic, since the hardness difference between tissues is represented through gray scales or colors in the elastic image, the distribution of gray scale or color in each local area may represent the hardness of the tissue of the local areas from another side.

Figure 5:
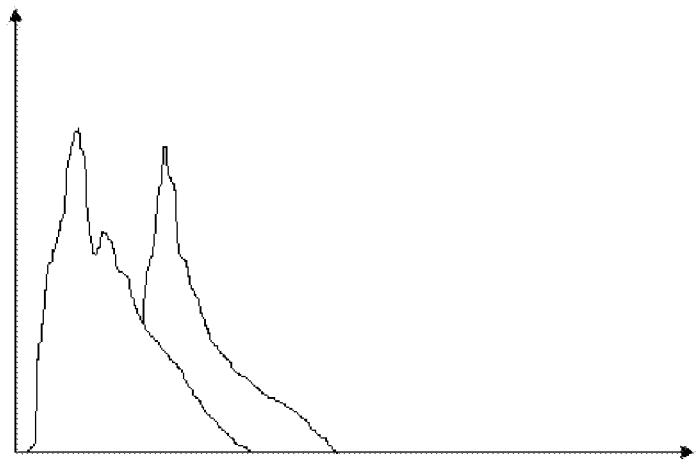
FIG. 5 is a schematic diagram of a histogram obtained in the shell analysis in one embodiment.

As shown in FIG. 5, the analysis unit may calculate the histogram statistic of the region of interest and the shell region, respectively, and draw the results in identical or different coordinates. The horizontal axis may represent graph used for elastic image mapping. The vertical axis may represent number or relative percentage of pixels counted in the statistical region. The horizontal axis of the histogram distribution diagram may be the graph of the current elastic image mapping (the system can provide various kinds of graphs for selection), the vertical axis may represent number or relative percentage of pixels counted in the statistical region. The narrower the range of histogram distribution diagram, the more concentrated the distribution of hardness of tissue in the statistical region will be. The more the histogram distribution diagram is close to a certain color on the horizontal axis, the more the hardness of tissue in the statistical region will be closer to a hardness corresponding to this color. Besides the histogram distribution diagram, the histogram result may include maximum value, minimum value, mean value, and standard deviation, etc. in the statistical sense.

In addition, as shown in FIG. 4, the system can draw a reference region additionally and calculate the histogram distribution of the shell region and the reference region.

In one embodiment, the system may further a storage device which stores the ultrasound image obtained by the imaging unit and/or the analysis result obtained by the analysis unit. The storage device may be any suitable storage device, such as any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like.

In the embodiments above, the elastic condition in the shell region may be obtained by analyzing the elasticity parameters of the shell region and the region of interest or the reference region. In one embodiment, the system may display the corresponding results according to the analysis parameters obtained by the analysis unit. For example, when the user choose to calculate the mean strain and ratio of the strains in the shell region and the region of interest, the calculated mean strain and ratio of the strains may be displayed on the display interface. In one example, when the user saves the current elastic image, the results of the analysis may be saved along with the current image. The user may also delete the current analysis results or change the position of the display of the analysis result, or perform other operation.

In one embodiment, an ultrasound elastography method may be provided. The method may include the following steps.

The transmitting/receiving unit 11 excites the ultrasound probe to transmit ultrasound pulses to the target to be inspected, and receive the ultrasound echoes reflected from the target through the ultrasound probe to obtain the ultrasound echo signals.

Thereafter, the imaging unit may process the received ultrasound echo signals to obtain the ultrasound images of the target and display the image obtained by the processing.

The analysis unit 15 may detect a region of interest and a shell region selected by the operator in the image, calculate elasticity parameters in a reference region and the shell region respectively, analyze the elasticity parameters in the reference region and the shell region, and output analysis results. The shell region may be a region obtained by subtracting the region of interest from an expanded region of the region of interest. Alternatively, the shell region may be a region obtained by subtracting a narrowed region of the region of interest from the region of interest. The reference region may be the region of interest. Alternatively, the reference region may be a detected region for reference selected by the operator in the image, or may be a region preset by the system.

In one embodiment, the two-dimensional image processing unit of the imaging unit 13 may process the received ultrasound echo signals to obtain a two-dimensional images of the target, and the two-dimensional image display unit may display the obtained two-dimensional images on the display device.

Figure 6:
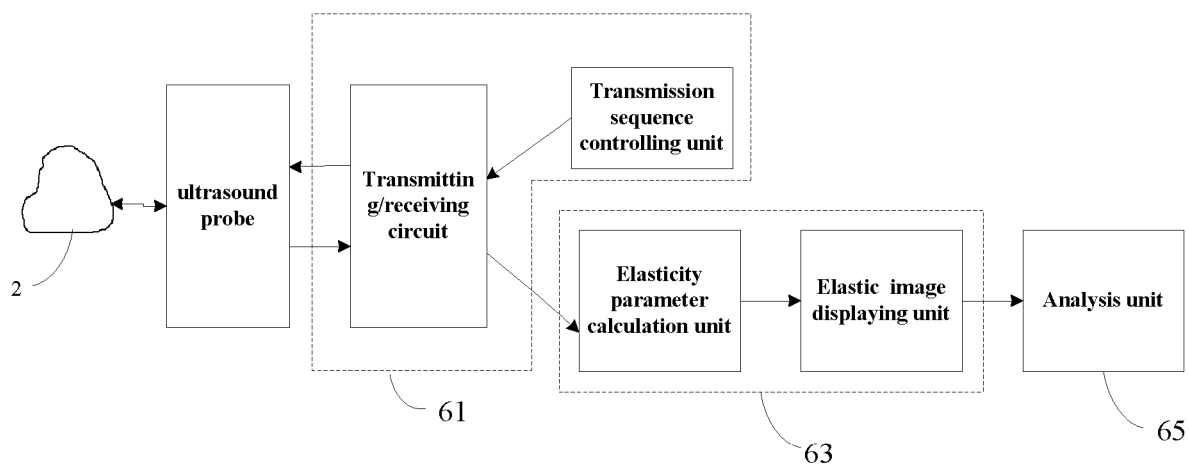
FIG. 6 is a structural schematic diagram of an ultrasound elastography system in one embodiment.

FIG. 6 shows the ultrasound elastography system in one embodiment. As shown in FIG. 6, the ultrasound elastography system may include a transmitting/receiving unit 61, an imaging unit 63, and an analysis unit 65. The transmitting/receiving unit 61 and the analysis unit 65 may be similar to the transmitting/receiving unit 11 and the analysis unit 15 in the embodiments above, respectively, which will not be described again herein.

In the imaging unit 63, an elasticity parameter calculation unit may process the ultrasound echo signals having been beam-formed to obtain the elasticity parameters representing the elasticity of the target and generate the elastic images of the target, and the elastic image display unit may display the obtained elastic images on a display device. In one embodiment, other processing may also be performed by the unit 63, such as signal amplification, analog/digital conversion and orthogonal decomposition, etc. In the present embodiment, selection of the region of interest and the shell region by the analysis unit 65 is performed on the elastic image.

In one embodiment, an ultrasound elastography method is provided, which may be similar to the method described in the embodiments above. The differences include, in the present embodiment, the imaging unit 63 may process the received ultrasound echo signals to calculate the elasticity parameters representing the elasticity of the target and generate the elastic images based on the elasticity parameters, and display the elastic image.

It should be understood that in the present embodiment the amount of calculation of elasticity parameters in the region of interest in the analysis unit 65 may be decreased.

The ultrasound elastography systems in the embodiments above may be combined. For example, in one embodiment, an ultrasound elastography system may include a transmitting/receiving unit, an imaging unit and a analysis unit. The transmitting/receiving unit and the analysis unit may be similar to the transmitting/receiving unit 11 and the analysis unit 15, or similar to the transmitting/receiving unit 61 and the analysis unit 65. The imaging unit may process the received ultrasound echo signals to generate the elasticity parameters to obtain the elastic image and generate the two-dimensional image. Thereafter, both or one of the elastic image and the two-dimensional image may be displayed.

In the ultrasound elastography methods or systems of the embodiments, firstly a region of interest and a shell region may be selected, that is, after images such as the two-dimensional image and/or the elastic image is obtained, the user can draw the region of interest and the shell region according to the elastic image or the two-dimensional image, manually or semi-automatically under system aiding. Thereafter, analysis may be performed on the shell region. During this process, the system may provide a series of selectable analysis parameters, and automatically analyzes and calculates related parameters in the shell region according to the parameters selected by the user. Thereafter, the analysis results of the shell region may be selectively displayed. For example, the system may displays the analysis results of the shell region according to the user's need, save the analysis results of the shell region together with the elastic image, or delete certain analysis result of the shell region, change the position of display of the analysis results of the shell region or perform other operations.

In the embodiments, the various units may be implemented hardware (such as circuit, processor, FPGA, GPU, CPU, general purpose IC, ASIC, various programmable devices, or other device), software, firmware and/or the combination thereof. The various units may be separate units. Alternatively, some of the units may be integrated in a single device.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. An ultrasound elastography system, comprising:
    an ultrasound probe;
    a transmitting and receiving unit that excites the ultrasound probe to transmit ultrasound pulses to a target to be inspected and receive ultrasound echoes from the target through the ultrasound probe to obtain ultrasound echo signals;
    an imaging unit that processes the ultrasound echo signals to obtain an ultrasound image of the target and display the ultrasound image;
    an input device configured to:
        allow a user to selectively draw a line around a region of interest in the ultrasound image corresponding to a tissue lesion, the line forming an inner perimeter of a shell region around the region of interest;
        allow the user to select a reference region in the ultrasound image that is outside of the region of interest; and
        allow the user to specify a thickness for the shell region,
        wherein the imaging unit automatically determines an outer perimeter for the shell region, such that the outer perimeter has a same shape as the inner perimeter, and a distance between the inner and outer perimeter is uniformly equal to the specified thickness;
    an analysis unit that:
        calculates a hardness difference between the shell region and the user-selected reference region; and
        generates at least one elastic image of the shell region and the reference region, wherein different colors of the at least one elastic image correspond to different tissue hardnesses; and
    a display interface that displays an indication of the hardness difference between the shell region and the user-selected reference region outside the region of interest or a hardness difference between the shell region and the region of interest, wherein the indication of hardness difference includes an elasticity histogram for the at least one elastic image of the shell region and the user-selected reference region, the elasticity histogram comprising a horizontal axis corresponding the different colors of the at least one elastic image and a vertical axis representing a number or relative percentage of pixels in each of the shell region and the user-selected reference region that correspond to each color of the at least one elastic image, wherein the elasticity histogram comparatively displays histogram data for the shell region and the user-selected reference region.

2. The system of claim 1, wherein the imaging unit comprises:
    an elasticity parameter calculation unit which processes the ultrasound echo signals to obtain elasticity parameters for the shell region and the reference region outside the region of interest and generates at least one elastic image of the shell region and the reference region based on the elasticity parameters, wherein different colors of each elastic image correspond to different tissue hardnesses according to the elasticity parameters; and
    an elastic image displaying unit which displays the at least one elastic image of the shell region and the reference region.

3. The system of claim 2, wherein the elasticity parameters comprise one or more of velocity of shear wave, velocity ratio of shear wave, Young's modulus, shear modulus, Young's modulus ratio, shear modulus ratio, elasticity modulus, elasticity modulus ratio, elasticity histogram statistic, and propagation distance of shear wave.

4. The system of claim 2, wherein displaying the indication of the hardness difference between the shell region and the user-selected reference region outside the region of interest comprises:

displaying an elasticity histogram for the at least one elastic image of the shell region and the reference region outside of the region of interest, the elasticity histogram comprising a horizontal axis corresponding to different colors of pixels in the at least one elastic image representing different tissue hardnesses and a vertical axis representing a number or relative percentage of pixels in each of the shell region and the reference region corresponding to each color of the at least one elastic image, wherein the elasticity histogram comparatively displays histogram data for shell region and the reference region.

5. The system of claim 4, wherein the analysis unit is further configured to:
calculate a mean strain of the region of interest over a period of time to generate a first strain-time curve; and
calculate a mean strain of the shell region over the period of time to generate a second strain-time curve; and
wherein the display interface is further configured to:
display the first strain-time curve, the second strain-time curve, and the indication of the hardness difference between the shell region and the user-selected reference region outside the region of interest.

6. The system of claim 1, wherein the imaging unit comprises:
a two-dimensional image processing unit which processes the ultrasound echo signals to obtain a two-dimensional ultrasound image of the target; and
a two-dimensional image displaying unit which displays the two-dimensional ultrasound image.

7. The system of claim 1, further comprising:
a display device which displays and analysis result obtained by the analysis unit; and/or
a storage device which stores the ultrasound image obtained by the imaging unit and/or the analysis result obtained by the analysis unit.

8. The system of claim 1, wherein the input device further receives a user selection of whether the shell region is to be obtained by expanding or narrowing of the region of interest.

9. The system of claim 1, wherein the input device receives the selection of a region of interest in response to the user drawing the region of interest on the ultrasound image.

10. The system of claim 1, wherein the imaging unit automatically draws the shell region on the ultrasound image according to the selected thickness.

11. The system of claim 1, wherein an analysis result includes a comparison of elasticity parameters calculated for the shell region and the elastic parameters calculated for the reference region.

12. The system of claim 11, wherein the analysis result comprises one or more of strain and strain ratio, strain-time curve, velocity of shear wave and velocity ratio of shear wave, elasticity modulus and elasticity modulus ratio, and elasticity histogram statistic between the region of interest and the shell region.

13. An ultrasound elastography method, comprising:
transmitting ultrasound pulses to a target to be inspected, and receiving ultrasound echoes from the target to obtain ultrasound echo signals;
processing the ultrasound echo signals to obtain an ultrasound image of the target and displaying the ultrasound image;
allowing a user to selectively draw a line around a region of interest in the ultrasound image corresponding to a tissue lesion, the line forming an inner perimeter of a shell region around the region of interest;
allowing the user to select a reference region in the ultrasound image that is outside of the region of interest;
allowing the user to select a thickness of the shell region;
automatically determining an outer perimeter for the shell region, such that the outer perimeter has a same shape as the inner perimeter, and a distance between the inner and outer perimeter is uniformly equal to the selected thickness;
calculating a strain or strain rate for the user-selected reference region outside of the region of interest;
calculating a strain or strain rate for the shell region;
calculating hardness difference between the shell region and the user-selected reference region outside the region of interest, wherein the hardness difference is calculated as a ratio of the strain or strain rate of the shell region and the strain or strain rate of the user-selected reference region;
calculating a mean strain of the region of interest over a period of time to generate a first strain-time curve;
calculating a mean strain of the shell region over the period of time to generate a second strain-time curve;
displaying the first strain-time curve, the second strain-time curve, and an indication of the hardness difference between the shell region and the user-selected reference region outside the region of interest;
generating at least one elastic image of the shell region and the reference region, wherein different colors of the at least one elastic image correspond to different tissue hardnesses; and
displaying an elasticity histogram for the at least one elastic image of the shell region and the reference region, the elasticity histogram comprising a horizontal axis corresponding the different colors of the at least one elastic image and a vertical axis representing a number or relative percentage of pixels in each of the shell region and the reference region that correspond to each color of the at least one elastic image, wherein the elasticity histogram comparatively displays histogram data for the shell region and the reference region.

14. The method of claim 13, wherein processing the ultrasound echo signals to obtain an ultrasound image of the target and displaying the ultrasound image comprises:
processing the ultrasound echo signals to obtain elasticity parameters representing elasticity of the target and generating an elastic image of the target based on the elasticity parameters; and
displaying the elastic image.

15. The method of claim 14, wherein the elasticity parameters comprise one or more of strain, strain ratio, strain rate, strain-time curve and elasticity histogram statistic.

16. The method of claim 14, wherein the elasticity parameters comprise one or more of velocity of shear wave, velocity ratio of shear wave, Young's modulus, shear modulus, Young's modulus ratio, shear modulus ratio, elasticity modulus, elasticity modulus ratio, elasticity histogram statistic, and propagation distance of shear wave.

17. The method of claim 13, wherein processing the ultrasound echo signals to obtain an ultrasound image of the target and displaying the ultrasound image comprises:
processing the ultrasound echo signals to obtain a two-dimensional ultrasound image of the target; and
displaying the two-dimensional ultrasound image.

18. The method of claim 13, further comprising:
displaying an analysis result indicating whether the tissue lesion is infiltrating the shell region.

19. An ultrasound elastography system, comprising:
an ultrasound probe;
a transmitting and receiving unit that excites the ultrasound probe to transmit ultrasound pulses to a target to be inspected and receives ultrasound echoes from the target through the ultrasound probe to obtain ultrasound echo signals;
an imaging unit that processes the ultrasound echo signals to obtain an ultrasound image of the target and displays the ultrasound image;
an input unit configured to:
  allow a user to selectively draw a line around a region of interest in the ultrasound image, the line forming an outer perimeter of a shell region around the region of interest; and
  allow the user to specify a thickness for the shell region, wherein the imaging unit automatically determines an inner perimeter for the shell region, such that the inner perimeter has a same shape as the outer perimeter, and a distance between the outer and inner perimeter is uniformly equal to the specified thickness;
an elasticity parameter calculation unit which processes the ultrasound echo signals to obtain elasticity parameters for the shell region and a user-selected or automatically-selected reference region outside of the region of interest and generates at least one elastic image of the shell region and the reference region based on the elasticity parameters, wherein different colors of the at least one elastic image correspond to different tissue hardnesses according to the elasticity parameters; and
an imaging unit that displays an elasticity histogram for the at least one elastic image of the shell region and the reference region, the elasticity histogram comprising a horizontal axis corresponding to the different colors of the at least one elastic image and a vertical axis representing a number or relative percentage of pixels in each of the shell region and the reference region that correspond to each color of the at least one elastic image, wherein the elasticity histogram comparatively displays histogram data for the shell region and the reference region.

20. The system of claim 19, wherein the elasticity parameters comprise one or more of strain, strain ratio, strain rate, strain-time curve and elasticity histogram statistic.

21. The system of claim 19, wherein the elasticity histogram comparatively displays histogram data for the shell region and the reference region in different sets of coordinates.

22. The system of claim 19, wherein the elasticity histogram comparatively displays histogram data for the shell region and the reference region in a same set of coordinates.

23. The system of claim 19, wherein:
the elasticity parameter calculation unit which processes the ultrasound echo signals to obtain elasticity parameters for the shell region and the region of interest and generates at least one elastic image of the shell region and the region of interest based on the elasticity parameters, wherein different colors of the at least one elastic image correspond to different tissue hardnesses according to the elasticity parameters; and
the imaging unit displays an elasticity histogram for the at least one elastic image of the shell region and the region of interest, the elasticity histogram comprising a horizontal axis corresponding to the different colors of the at least one elastic image and a vertical axis representing a number or relative percentage of pixels in each of the shell region and the region of interest that correspond to each color of the at least one elastic image, wherein the elasticity histogram comparatively displays histogram data for the shell region and the region of interest.

* * * * *

UNITED STATES PATENT AND TRADEMARK OFFICE
CERTIFICATE OF CORRECTION

PATENT NO. : 11,564,658 B2  
APPLICATION NO. : 15/894476  
DATED : January 31, 2023  
INVENTOR(S) : Shuangshuang Li and Jianqiao Zhou Page 1 of 1

It is certified that error appears in the above-identified patent and that said Letters Patent is hereby corrected as shown below:

On the Title Page

Item (73) Assignees, add the following:
--RUIJIN HOSPITAL, SCHOOL OF MEDICINE, SHANGHAI JIAOTONG UNIVERSITY, Shanghai (CN)--

Signed and Sealed this  
Twenty-ninth Day of October, 2024

Katherine Kelly Vidal  
*Director of the United States Patent and Trademark Office*